US010768158B2

(12) United States Patent
Vellaisamy et al.

(10) Patent No.: US 10,768,158 B2
(45) Date of Patent: Sep. 8, 2020

(54) ELECTROCHEMICAL DETECTOR

(71) Applicant: City University of Hong Kong, Kowloon (HK)

(72) Inventors: A. L. Roy Vellaisamy, Kowloon (HK); Chi-Chung Yeung, Sheung Shui (HK); Michael H. W. Lam, Kowloon (HK); Siu-Chuen Lau, Kowloon (HK); Kam-Sing Chung, Kowloon (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 15/364,541

(22) Filed: Nov. 30, 2016

(65) Prior Publication Data

US 2018/0149632 A1    May 31, 2018

(51) Int. Cl.
| *G01N 33/12* | (2006.01) |
| *G01N 27/12* | (2006.01) |
| *B05D 1/00* | (2006.01) |
| *G01N 27/416* | (2006.01) |
| *G01N 33/02* | (2006.01) |

(52) U.S. Cl.
CPC ............. *G01N 33/12* (2013.01); *B05D 1/005* (2013.01); *G01N 27/126* (2013.01); *G01N 27/416* (2013.01); *G01N 33/02* (2013.01)

(58) Field of Classification Search
CPC ...... G01N 33/12; G01N 33/02; G01N 27/416; B05D 1/005
See application file for complete search history.

(56) References Cited

U.S. PATENT DOCUMENTS

| 8,384,409 | B2 | 2/2013 | Kummel et al. |
| 9,410,970 | B2 | 8/2016 | Tian et al. |
| 2014/0042494 | A1 | 2/2014 | Han et al. |
| 2014/0197405 | A1 | 7/2014 | Vellaisamy et al. |
| 2016/0025517 | A1 | 1/2016 | Giedd et al. |

FOREIGN PATENT DOCUMENTS

JP    2000241403 A    9/2000

OTHER PUBLICATIONS

Zayats, Maya, et al. "Imprinting of specific molecular recognition sites in inorganic and organic thin layer membranes associated with ion-sensitive field-effect transistors." Tetrahedron 58.4 (2002): 815-824.*

Liang, Rongning, Ruiming Zhang, and Wei Qin. "Potentionnetric sensor based on molecularly imprinted polymer for determination of melamine in milk." Sensors and Actuators B: Chemical 141.2 (2009): 544-550.*

(Continued)

*Primary Examiner* — Robert J Eom
(74) *Attorney, Agent, or Firm* — Renner Kenner Greive Bobak Taylor & Weber

(57) ABSTRACT

An electrochemical detector includes a substance selection layer disposed on a semiconductor layer, and the substance selection layer is arranged to interact with a target substance so as to alter an electrical characteristic of the semiconductor layer. A method for fabricating an electrochemical detector is also disclosed.

25 Claims, 11 Drawing Sheets

(56) References Cited

OTHER PUBLICATIONS

Pietrzyk, Agnieszka, et al. "Molecularly imprinted polymer (MIP) based piezoelectric microgravimetry chemosensor for selective determination of adenine." Biosensors and Bioelectronics 25.11 (2010): 2522-2529.*
Sontimuang, Chonlatid, Roongnapa Suedee, and Franz Dickert. "Interdigitated capacitive biosensor based on molecularly imprinted polymer for rapid detection of Hev b1 latex allergen." Analytical biochemistry 410.2 (2011): 224-233. (Year: 2011).*
Bobacka, J., "Conducting Polymer-Based Solid-State Ion-Selective Electrodes", Electroanalysis, vol. 18, pp. 7-18.
Basozabal I., et al., "Direct potentiometric quantification of histamine using solid-phase imprinted nanoparticles as recognition element." Biosensors and Bioelectronics, vol. 58, 2014, pp. 138-144.
Pietrzyk A., et al., "Selective Histamine Piezoelectric Chemosensor Using a Recognition Film of the Molecularly Imprinted Polymer of Bis(bithiophene) Derivatives." Anal. Chem., vol. 81, 2009, pp. 2633-2643.

* cited by examiner 2-(4-(di([2,2'-bithiophen]-5-yl)methyl)phenyl)-5,5-dimethyl-1,3,2-dioxaborinane, 18-(di([2,2'-bithiophen]-5-yl)methyl)-2,3,5,6,8,9,11,12,14,15-decahydrobenzo[ b][1,4,7,10,13,16]hexaoxacyclooctadecine,

ELECTROCHEMICAL DETECTOR

TECHNICAL FIELD

The present invention relates to an electrochemical detector, although not exclusively, to an electrochemical detector for detecting biogenic amines, indicative of a quality of a food being tested.

BACKGROUND

Food poisoning is one of the most serious public health problems in cities around the world. Various toxins in food may affect the health of the consumers. Therefore, the quality of food must be examined to ensure that some poisonous or hazardous toxins do not exist in food.

The concentration of toxins may be determined by using testing agents. The traditional chemical testing approaches are time consuming and may not response promptly. Alternatively, material characterization techniques in laboratories may be used to analyse the concentration of a target substance and even the composition of a testing sample. Although the results may be very accurate and sensitive, these techniques used in laboratories may not be suitable for daily applications which may require prompt and low-cost testing results.

SUMMARY OF THE INVENTION

In accordance with a first aspect of the present invention, there is provided an electrochemical detector comprising a substance selection layer disposed on a semiconductor layer, wherein the substance selection layer is arranged to interact with a target substance so as to alter an electrical characteristic of the semiconductor layer.

In an embodiment of the first aspect, the target substance includes an amine.

In an embodiment of the first aspect, the target substance includes a biogenic amine.

In an embodiment of the first aspect, the substance selection layer includes a polymer layer arranged to accommodate at least one molecule of the target substance.

In an embodiment of the first aspect, the polymer layer includes a plurality of voids each arranged to accommodate each of the at least one molecule of the target substance.

In an embodiment of the first aspect, each of the plurality of voids includes a structure matching with a molecular structure of the at least one molecule.

In an embodiment of the first aspect, the plurality of voids is selective to the target substance.

In an embodiment of the first aspect, the polymer layer includes a molecular imprinted polymer.

In an embodiment of the first aspect, the molecular imprinted polymer includes a plurality of polymer particles each having a size of around 50 µm.

In an embodiment of the first aspect, the substance selection layer is electrically conductive.

In an embodiment of the first aspect, the substance selection layer is electrically non-conductive.

In an embodiment of the first aspect, the electrical characteristic of a combination of the substance selection layer and the semiconductor layer is altered when the polymer layer accommodates the at least one molecule.

In an embodiment of the first aspect, an electrical impedance of the combination of the substance selection layer and the semiconductor layer is altered.

In an embodiment of the first aspect, the semiconductor layer includes at least one of an organic semiconductor, a polymer semiconductor, small molecules, an oxide-based semiconductor and a silicon-based semiconductor.

In an embodiment of the first aspect, the electrochemical further comprises a substrate under the semiconductor layer and at an opposite side of the substance selection layer disposed thereon.

In an embodiment of the first aspect, the substrate is a flexible substrate.

In an embodiment of the first aspect, the substrate includes insulating material and/or semiconductor, and wherein the insulating material further includes at least one of polymer, glass and ceramic.

In an embodiment of the first aspect, the electrochemical detector further comprises at least two electrodes disposed on or above the semiconductor layer.

In an embodiment of the first aspect, the semiconductor layer, the substance selection layer and the electrodes are based on organic materials and/or metal oxide.

In an embodiment of the first aspect, the semiconductor layer has a thickness of 10 nm-200 nm.

In an embodiment of the first aspect, the at least two electrodes are spaced at a distance in a range of around 50 µm to 1000 µm.

In accordance with a second aspect of the present invention, there is provided a method of fabricating an electrochemical detector in accordance with the first aspect, comprising the steps of: depositing the semiconductor layer on a substrate; and depositing the substance selection layer on the semiconductor layer.

In an embodiment of the second aspect, the step of depositing the substance selection layer on the semiconductor layer comprise the steps of: fabricating a combination of a molecular-imprinted polymer and a molecular template of the target substance using a polymerization process; extracting and removing the molecular template from the molecular-imprinted polymer; and depositing the molecular-imprinted polymer on the substrate.

In an embodiment of the second aspect, the step of depositing the substance selection layer on the semiconductor layer further comprises the step of grounding and sieving the combination of the molecular-imprinted polymer and the molecular template to obtain a plurality of polymer particles each having a size of around 50 µm.

In an embodiment of the second aspect, the method further comprises the step of depositing a layer of electrical conductive material defining at least one electrode on or above the semiconductor layer.

In an embodiment of the second aspect, the steps of depositing the semiconductor layer, the substance selection layer and/or the layer of electrical conductive material involve a solution process.

In an embodiment of the second aspect, the solution process involve spin coating and/or printing, wherein the solution process of printing further includes pad printing and/or silk screening.

In accordance with a third aspect of the present invention, there is provided a method of detecting a target substance, comprising the steps of: exposing an electrochemical detector in accordance with the first aspect to the target substance; applying a voltage and/or a current bias across the at least two electrodes; and determining an amount of target substance detected based on a current-voltage characteristic of the electrochemical detector exposed to the target substance.

In an embodiment of the third aspect, the step of determining an amount of target substance detected based on the current-voltage characteristic of the electrochemical detector exposed to the target substance includes determining a change of electrical resistance across the at least two electrodes of the electrochemical detector.

In an embodiment of the third aspect, wherein the detected amount of target substance is further associate to a quality of food.

BRIEF DESCRIPTION OF THE DRAWINGS

Embodiments of the present invention will now be described, by way of example, with reference to the accompanying drawings in which.

DETAILED DESCRIPTION OF THE PREFERRED EMBODIMENT

The inventors have, through their own research, trials and experiments, devised that biogenic amines are organic compounds that may form as a result of bacterial action (e.g. decarboxylation reaction of precursor amino acids) with the availability of free amino acids. There are numerous bacterial genera with the amino acid decarboxylase capability naturally present in food, intentionally added or introduced by contamination. The amount of biogenic amine formed may depend on the food composition and the type of bacterial genera present in the matrix.

The presence of certain concentration of biogenic amines in food will cause health problems due to its physiological and toxic effects. Therefore, the quality of food can be reflected by the amount of biogenic amines in food. For example, histamine, putrescine, cadaverine, tyramine, spermine, and spermidine may be found in rotten food, especially in fishes. A Chemical Quality Index (QI) based on the concentration of these amines may be used to express the quality of fish.

To determine the presence and/or concentration of these toxic substances, high-performance liquid chromatography-mass spectrometry (HPLC-MS) may be applied to detect biogenic amines, however the instrument is big in size and expensive, and it requires a trained person to operate. Furthermore, before injecting the extracts form fishes into the HPLC-MS, a number of special treatments are required. As a result, the QI cannot be easy applied to the public.

In daily applications, cheap and disposable sensors are preferable. Preferably, thin film based sensors have high sensitivity and selectivity, which require only simple device fabrication process. In addition, thin film devices have may be printed in large areas during production to reduce the fabrication cost.

Figure 1:
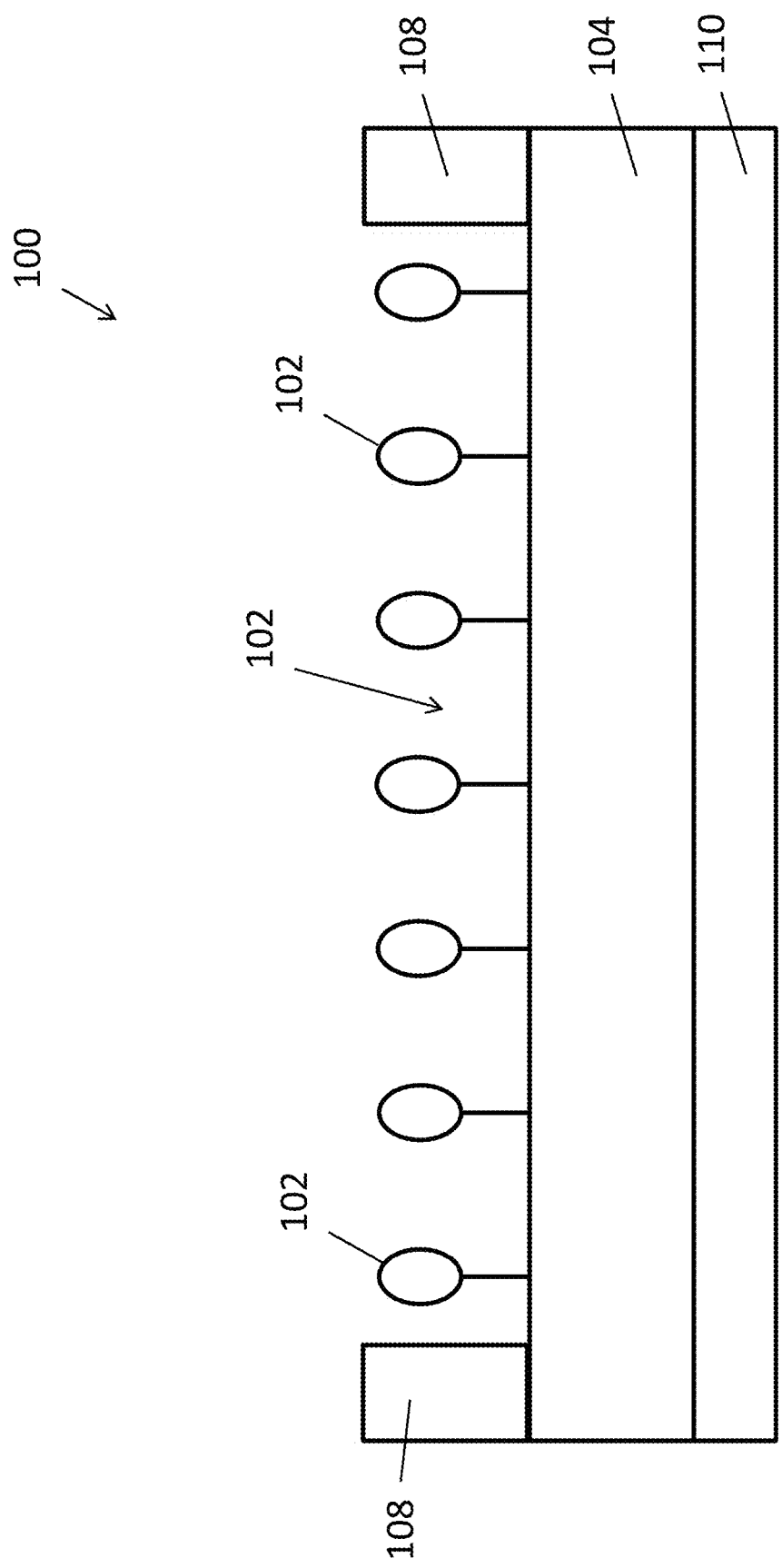
FIG. 1 is a side view of an electrochemical detector in accordance with one embodiment of the present invention.

With reference to FIG. 1, there is shown an example embodiment of an electrochemical detector 100 comprising a substance selection layer 102 disposed on a semiconductor layer 104, wherein the substance selection layer 102 are arranged to interact with a target substance 106 so as to alter an electrical characteristic of the semiconductor layer 104.

In this embodiment, the electrochemical detector 100 comprises a substance selection layer 102, which may include one or more chemical receptors or chemical structures arranged to interact with other chemical substances when exposed in a testing environment. For example, a gaseous target substance 106 may be found in air such that the receptors 102A may interact with the gaseous target substances 106 in air when the electrochemical detector 100 is placed in air. Alternatively, a liquid base target substance 106 may be applied on the electrochemical detector 100 such that the receptors 102A may contact with the target substance 106 and subsequently interact with the target substance 106.

Preferably, the substance selection layer 102 may include a polymer layer. The polymer layer 102 may have a composition or a structure for accommodating a molecule or a portion of a molecule of the target substance, such that electrical characteristic of the semiconductor layer which is in contact with the polymer layer may be altered. For example, the polymer layer 102 may include a plurality of voids 102A each arranged to accommodate each of the at least one molecule of the target substance 106. Thus the voids 102A may operate as "receptors" which may interact with the target substance 106

In addition, the plurality of voids 102A may be selective to the target substance 106, thus the substance selection layer 102 may only interact with the selected target substance 106. Preferably, the polymer layer may include a molecular imprinted polymer (MIP), in which each of the plurality of voids 102A may include a structure matching with a molecular structure of the at least one molecule of the target substance 106, such that only matching molecules may fill up the voids 102A in the polymer layer 102, and the polymer layer 102 will not interact with substance with any molecular structures which do not match with the molecular imprinted structure.

In one example embodiment, the target substance 106 includes an amine or a biogenic amine, and the MIP is selective to only interact with such amine or biogenic amine.

Figure 2A:
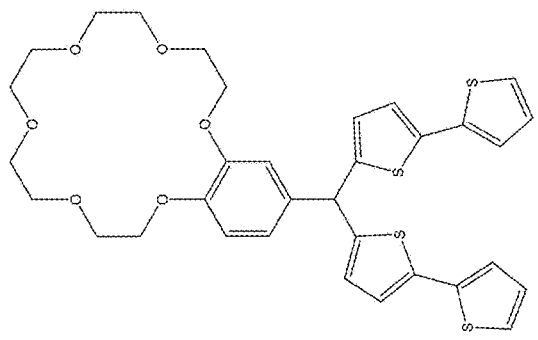
FIGS. 2A to 2B and 3A to 3B are structure formulas of monomers which are used in a fabrication process of a molecular imprint polymer.

With reference to FIGS. 2A to 3B, there is shown some example monomers for used in producing such molecular imprinted polymer 102. Based on different monomer used in producing the molecular imprinted polymer, the target substance may be electrically conductive or non-conductive. For example, precursors of the MIP may include a mixture of monomers of (4-(di([2,2'-bithiophen]-5-yl)methyl)phenyl)-5,5-dimethtyl-1,3,2-dioxaborinane and 18-(di([2,2'-bithiophen]-5-yl)methyl)-2,3,5,6,8,9,11,12,14,15-decahydrobenzo[b][1,4,7,10,13,16]hexaoxacylooctadecine as shown in FIGS. 2A and 2B respectively, a template of the target substance (e.g. 1,4-diaminobutane, Putrescine) and other necessary substances in a polymerization process, and a conductive MIP layer is produced after polymerization and the extraction of the template of the target substance.

Figure 3A:
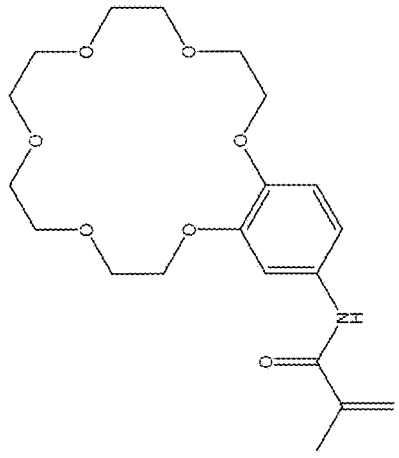
Figure 3B:
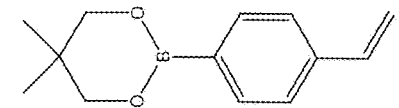

Alternatively, precursors of the MIP may include a mixture of monomers of 5,5-dimethyl-2-(4-vinylphenyl)-1,3,2-dioxaborinane and N-(2,3,5,6,8,9,11,12,14,15-decahydrobenzo[b][1,4,7,10,13,16]hexaoxacyclooctadecin-18-yl)

methacrylaminde as shown in FIGS. 3A and 3B respectively, a template of the target substance (e.g. 1,4-diaminobutane, Putrescine), and other necessary substances such as a cross-linker, and a non-conductive MIP layer 102 is produced after a polymerization process and the extraction of the template of the target substance. More detailed examples of the preparation of the MIP layer 102 will be discussed in this disclosure.

Figure 4A:
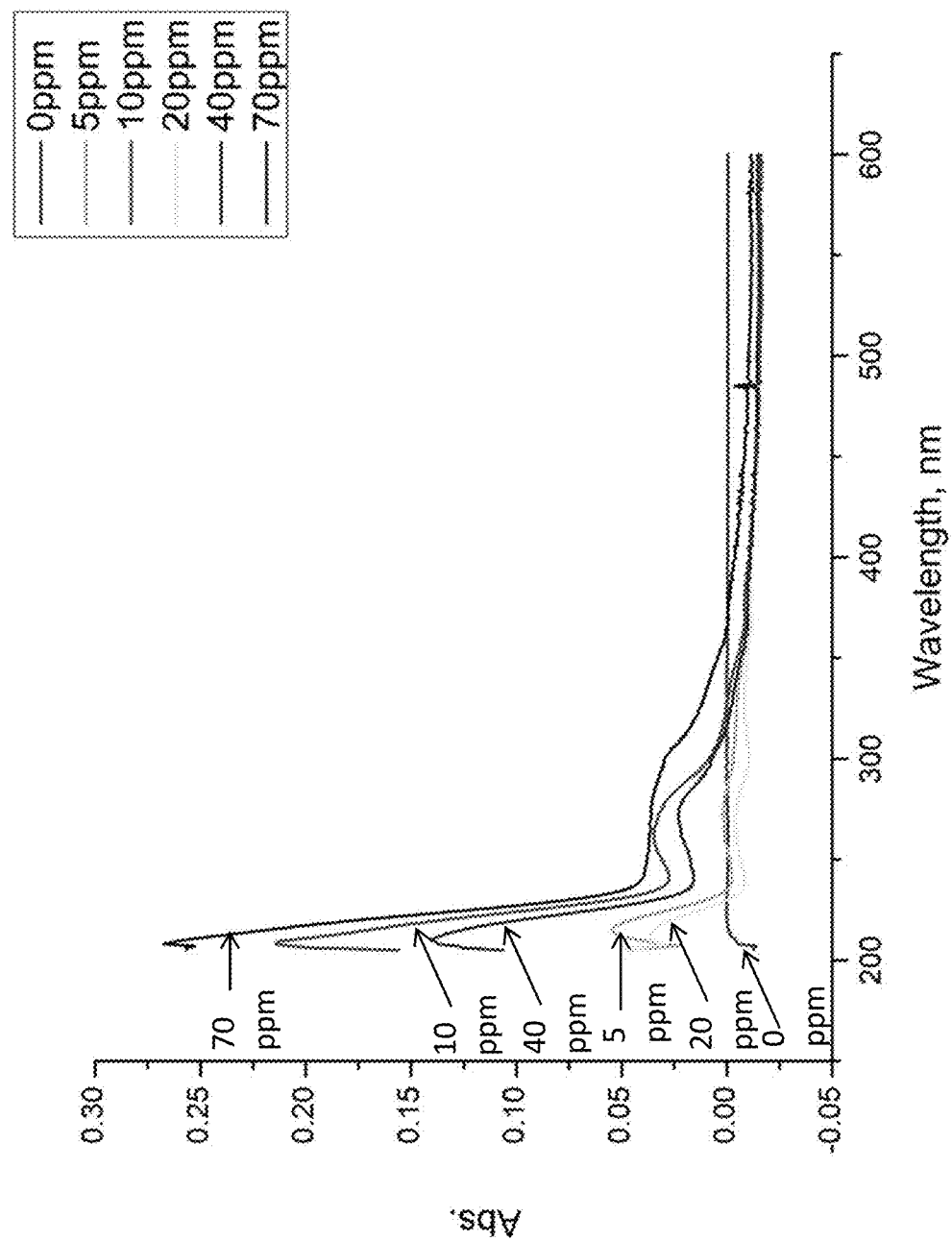
FIGS. 4A and 4B are plots showing UV responses of a molecular imprint polymer layer interacting with a target substance.
Figure 4B:
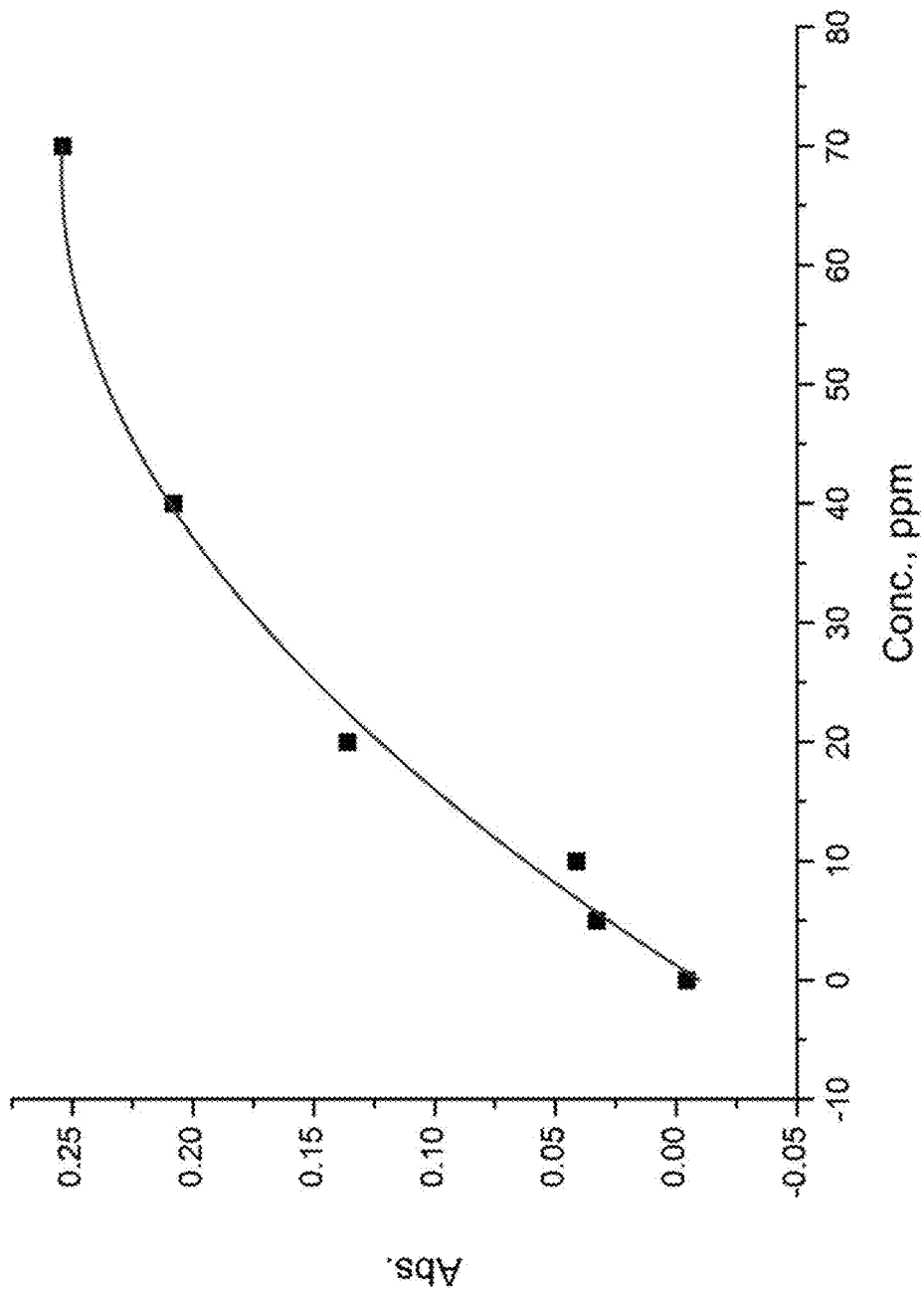

The MIP layer 102 includes a plurality of voids 102A which may accommodate the molecules of the target substance. Referring to FIGS. 4A and 4B, there is shown the binding capacity of the MIP in different concentration of putrecine solution. The UV spectrum as shown in FIG. 3A suggests that the MIP shows different UV spectrums when interacting with various concentration of putrescine solution. Referring to FIG. 3B, it is shown that the linear range is from 0 ppm to 40 ppm.

Figure 5:
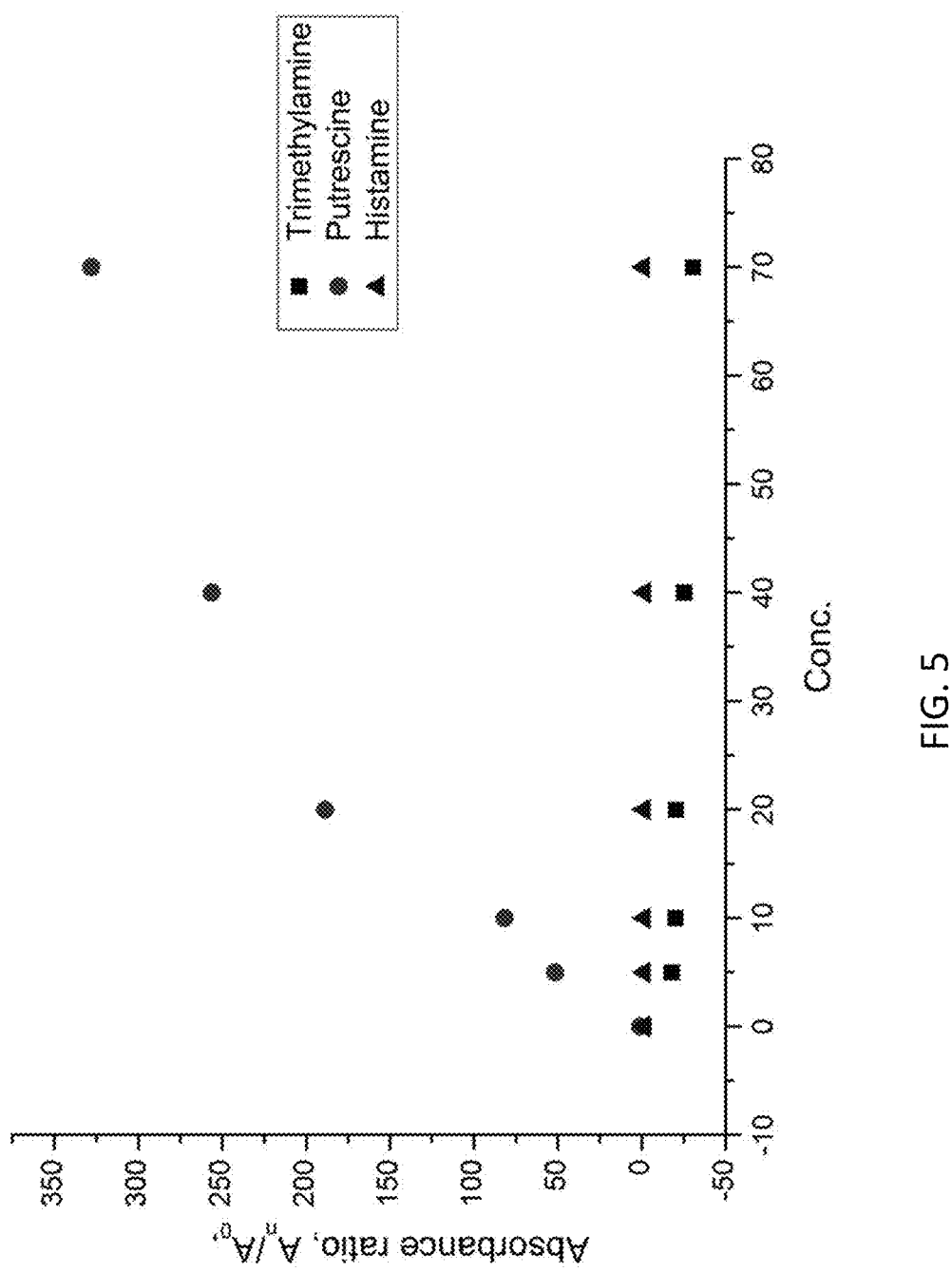
FIG. 5 is a plot showing the selectivity performance of the molecular imprint polymer layer.
Figure 6:
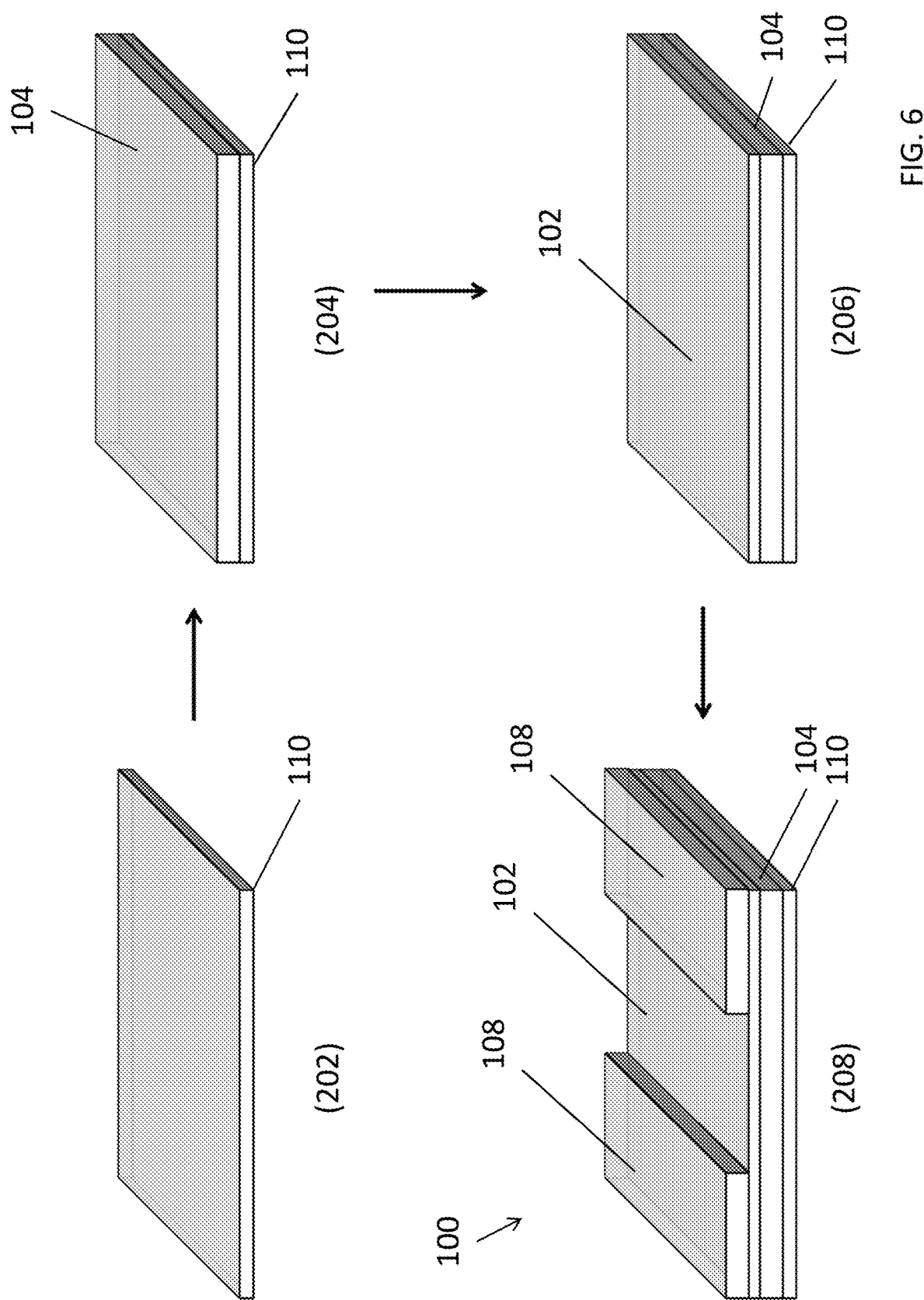
FIG. 6 is an illustration showing a process flow of a fabrication of the electrochemical detector of FIG. 1.

With reference to FIG. 5, it is shown that the MIP is selective to the target substance, i.e. putrescine according the above example embodiment. In this example, histamine, putrescine and cadaverine in different concentrations were tested with the prepared MIP layer. Referring to the Figure, the MIP is only responsive to putrescine but not to histamine or cadaverine, which suggests that the voids 102A may only be filled with putrescine but not with substances with incompatible molecular structures.

The electrochemical detector 100 also comprises a semiconductor layer 104. The semiconductor layer 104 has a unique electrical characteristics which allows/disallows electric current or electrons to pass through under different conditions. For example, the semiconductor may be arranged to allow electric current to pass through when a target substance 106 is detected and/or to disallow electric current to pass through when the concentration of the target substance 106 is below a predetermined value.

The semiconductor layer 104 includes different semiconductor material, such as an organic semiconductor, a polymer semiconductor, small molecules, an oxide-based semiconductor and/or a silicon-based semiconductor. Different semiconductor material may be selected for different fabrication processes, matching with the substrate layer and/or the MIP layer, or other factors such as required performance such as sensitivity, response time, detection range, etc.

To facilitate the measurement of an electric current passing through the semiconductor layer 104, the electrochemical detector 100 may comprise two electrodes 108 on or above the semiconductor layer 104. The electrodes 108 may be deposited directly on the semiconductor layer 104 and contact with the semiconductor layer 104 which may enhance the electrical conductivity at the electrode-to-semiconductor interface. Alternatively, the electrodes 108 may be deposited on the MIP layer 102 in some device structures.

Preferably, two or more electrodes 108 may be deposited on or above the semiconductor layer 104 to facilitate the measurement. The electrodes 108 may include one or more metal pads defined on or above the semiconductor layer 104. Alternatively, the electrodes 108 may include any electrically conductive material such as but not limited a metal, a doped semiconductor, or a conductive oxide.

The electrochemical detector 100 may be fabricated on a substrate 110, as shown in FIG. 1, the substrate 110 is substantially under the semiconductor layer 104 and at an opposite side of the MIP layer. The substrate 110 may consist of a material which provides additional mechanical strength to the entire structure of the electrochemical detector 100. For example, this may include a material such as a polymer, glass or ceramic. The substrate 110 may be a flexible substrate 110 such as a polyethylene terephthalate (PET) substrate, or alternatively a non-flexible substrate in some other structures. In some example embodiments, the substrate 110 is the semiconductor layer 104 (such as a silicon substrate), which includes a necessary stiffness for supporting the entire structure of the electrochemical detector 100 as well as the required semiconductor material with the desired electrical properties.

Optionally, all the deposited layers of material of the electrochemical detector 100, including the layer of substance selection layer, the semiconductor layer 104 and the electrodes 108 are based on organic material. This may be advantageous for some preferred fabrication processes which may only requires low-temperature processes and/or solution process, such that the fabrication complexity and cost may be kept low.

With reference to FIG. 2, the fabrication of the electrochemical detector 100 may comprise four main steps or processes. Firstly, at step 202, a substrate 110 such as a flexible PET substrate or a glass substrate is cleaned according to a standing cleaning procedure. Secondly, at step 204, the semiconductor thin film layer is deposited on the surface of the substrate by spin coating method and solvent annealing. Thirdly, at step 206, biogenic amines selective material, which can be conductive or non-conductive, is mixed with acetonitrile (1 mg/mL) and spin coated on the top of the semiconductor layer.

In step 206, other solvent, such as but not limited to water, acetone, methanol, ethanol, propanol, butanol, ethyl acetate, ethylene glycol, benzene, chloroform, tetrahydrofuran, t-butyl alcohol, cyclohexane, chloroethane, diethyl ether, diethyl glycol, dimethyl sulfoxide or any other solvent suitable for dissolving the MIP polymer particles may be used. The solvent may then be driven away in a following drying process so as to form the MIP layer.

Preferably, the process includes fabricating a combination of a molecular-imprinted polymer and a molecular template of the target substance using a polymerization process. As discussed earlier, the voids 102A or the recognition site in this MIP may be created by the cooperation of two different monomers which may be dioxaborinane based and 18-crown-6 based. The backbone of these monomer can either be conductive (e.g. bis(bithiophene) based) or non-conductive (e.g. CC Double Bond based).

Figure 2B:
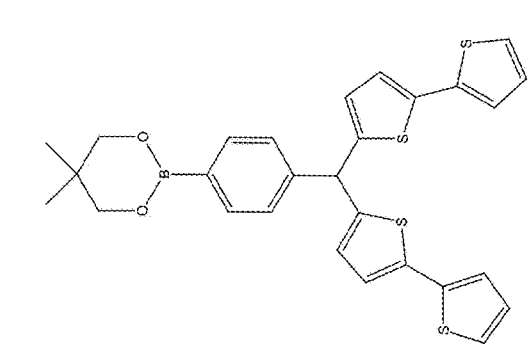

In one example embodiment, conductive biogenic amines selective material may be first prepared by mixing 1 mmol monomers of (4-(di([2,2'-bithiophen]-5-yl)methyl)phenyl)-5,5-dimethtyl-1,3,2-dioxaborinane and 18-(di([2,2'-bithiophen]-5-yl)methyl)-2,3,5,6,8,9,11,12,14,15-decahydrobenzo[b][1,4,7,10,13,16]hexaoxacylooctadecine as shown in FIGS. 2A and 2B respectively, 0.5 mmol MIP template (1,4-diaminobutane, Putrescine), 1 mmol tetrabutylammonium perchlorate and 1 mmol trifluoroacetic acid in 10 mL acetonitrile (ACN). After the solution is well mixed, the solution is degassed by nitrogen, and a working electrode (ITO glass) may be place into the solution for preparing the MIP film via the electropolymerization. The MIP film may be fabricated by potential cycling at 50 mV/s in the potential rage 0.5-1.5 V for 300 cycles. The MIP film may then be rinsed with ACN to remove the supporting electrolyte, and the MIP template is then extracted and removed by washing with 0.01 M NaOH until no templates could be detected in the extractant. Then, the film may be dried under nitrogen atmosphere. The dried film may be agitated by sonication in ACN for 2 hours, and the suspension is then filtered out. The residual solution was removed under vacuum, and the residue was weighted. A suitable of ACN may be added to prepare the stock solution (e.g. 1 mg MIP/1 mL ACN).

Alternatively, non-conductive biogenic amines selective material may be prepared by mixing 1 mmol monomers of 5,5-dimethyl-2-(4-vinylphenyl)-1,3,2-dioxaborinane and N-(2,3,5,6,8,9,11,12,14,15-decahydrobenzo[b][1,4,7,10,13,16]hexaoxacyclooctadecin-18-yl)methacrylaminde as shown in FIGS. 3A and 3B respectively, 5 mmol cross-linker (e.g. trimethylolpropane trimethacrylate), 0.1 mmol 2-hydroxy-4'-(2-hydroxyethoxy)-2-methylpropiophenone, and 0.1 mmol template (1,4-diaminobutane, Putrescine) in 5 mL acetonitrile (ACN). After the solution is well mixed, the solution may be degassed by nitrogen, the solution may be exposed under UV lamp (365 nm in wavelength) for an hour to initiate the MIP polymerization. The polymerization process may be kept for 24 hours. After that, the MIP may be filtered, washed and dried under nitrogen atmosphere. Then, MIP was ground and sieved to such that the MIP includes a polymer particles each having a size of around 50 µm. The template may be extracted out from the MIP by Soxhelt extraction for 24 hours with ammonium hydroxide and methanol mixture (1:9) followed by methanol for another 24 hours. Finally, the MIP powder may be dried under a nitrogen atmosphere.

Alternatively, the size of MIP particles may have a different value which may effectively alter the response time of the electrochemical detector.

Depending on different applications and/or measurement requirements, the abovementioned conductive or non-conductive MIP may be deposited on the surface of the semiconductor layer in step 206 as discussed earlier.

The thickness of the semiconductor layer 104 and the MIP layer 102 may be around 50 nm (or any thickness of 10 nm-200 nm) and 50-100 µm respectively. These thickness values may vary in different designs so as to optimize a number of parameters such as any process variations, the electrical resistance value of the semiconductor layer 104 and/or the MIP layer, the contact resistance between the electrodes 108 and the semiconductor, the electrical effect of the substance selection layer 102 and/or the semiconductor layer during the interaction, etc.

Finally, at step 208, two electrodes 108 such as copper metal films or other conductive material are deposited on the surface of the MIP layer. In an alternative embodiment, the MIP layer 102 may be patterned such that electrodes 108 may contact directly with the semiconductor layer 104. The electrodes 108 may be deposited by conformal deposition of a layer of conductive material using spin coating and/or printing followed by a subsequent patterning of the layer of conductive material. Alternatively, the electrodes 108 may be patterned when it is deposited on or above the semiconductor layer 104 using any printing techniques, for example, two interdigitated metal electrodes may be deposited and patterned on the surface of the MIP layer 102 by thermal evaporation through a shadow mask.

Preferably, the at least two electrodes 108 are spaced at a distance in a range of around 50 µm 100 µm. This effectively affects the area of the MIP layer 102 exposed to and interacting with the target substance 106, and the electrical resistance of the semiconductor and/or the MIP layer 102 between the two electrodes 108. These parameters in turns affect the sensitivity and performance of the electrochemical detector 100.

Preferably, the entire fabrication process is based on solution processes (such as spin coating and/or printing), and each of the deposited layers is organic material based. This allows the scale of the fabrication of the electrochemical detector 100 to be scaled up easily, such as using a roll-to-roll fabrication process with various printing technologies. These solution processes may only require low-temperature equipment and does not involve any vacuum processes which further minimize the cost of the fabrication of the electrochemical detector 100.

Figure 7A:
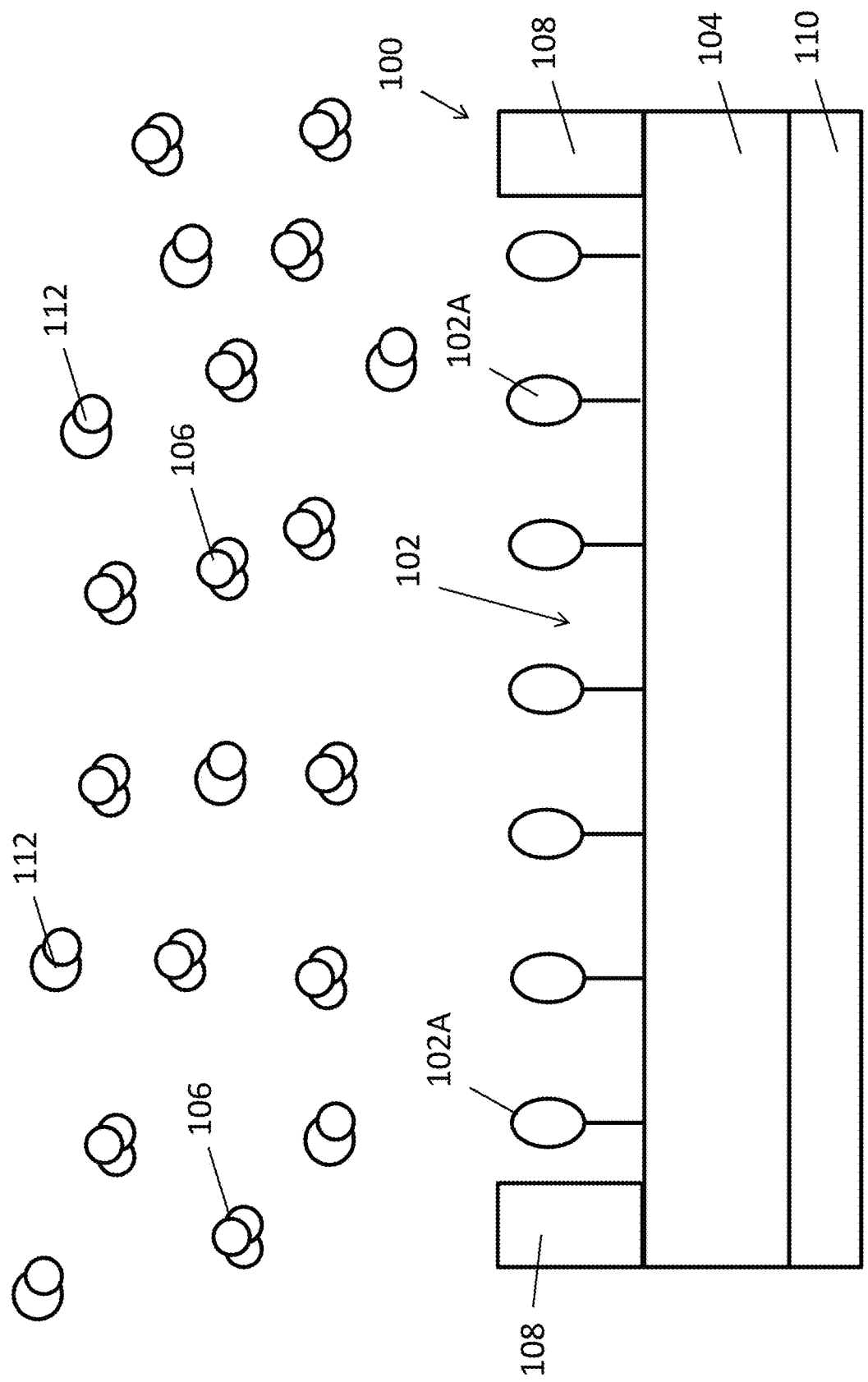
FIG. 7A is an illustration of an electrochemical detector of FIG. 1 exposed to a target substance.
Figure 7B:
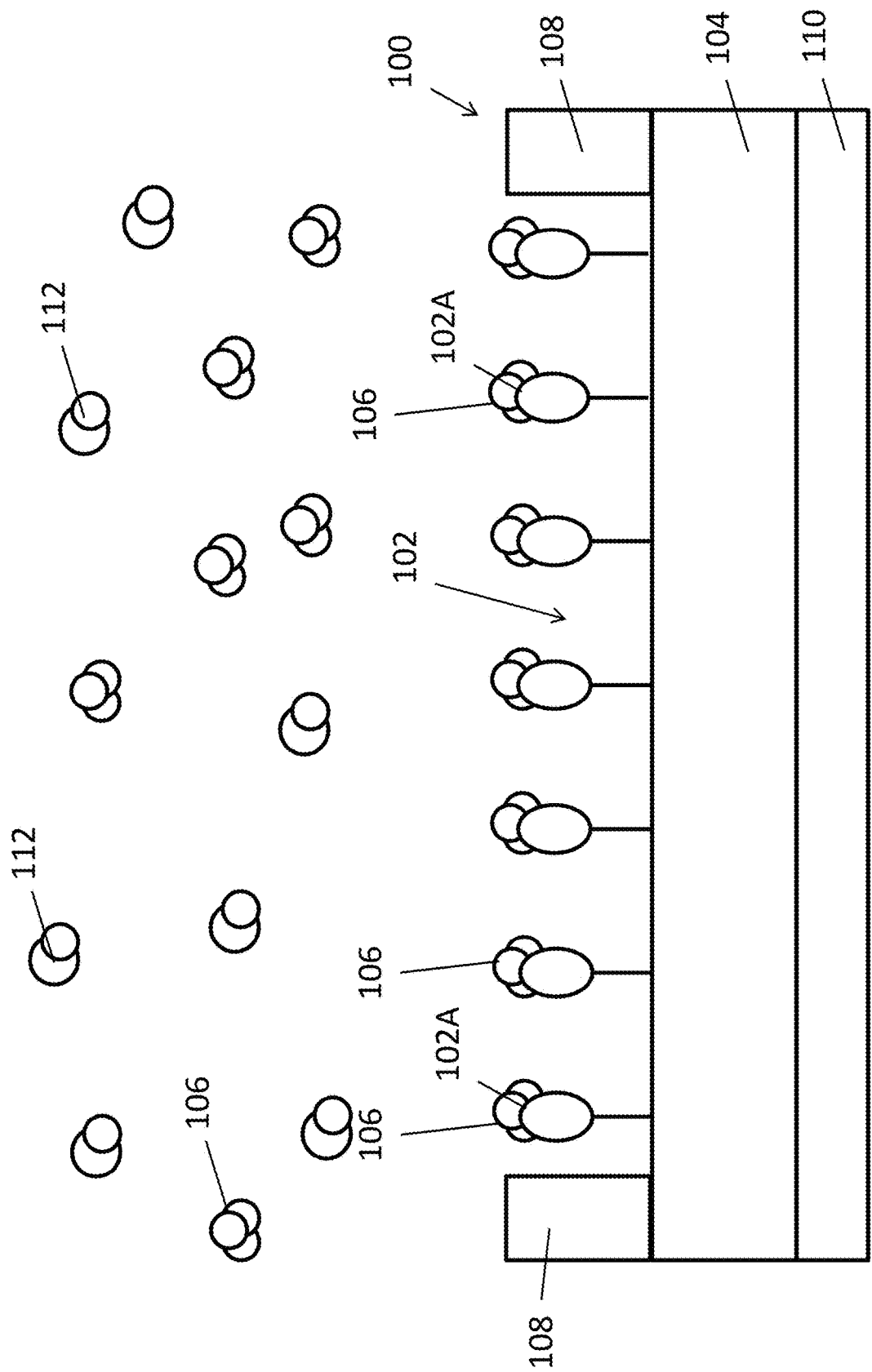
FIG. 7B is an illustration of an electrochemical detector of FIG. 7A selectively interacting with a target substance.
Figure 8:
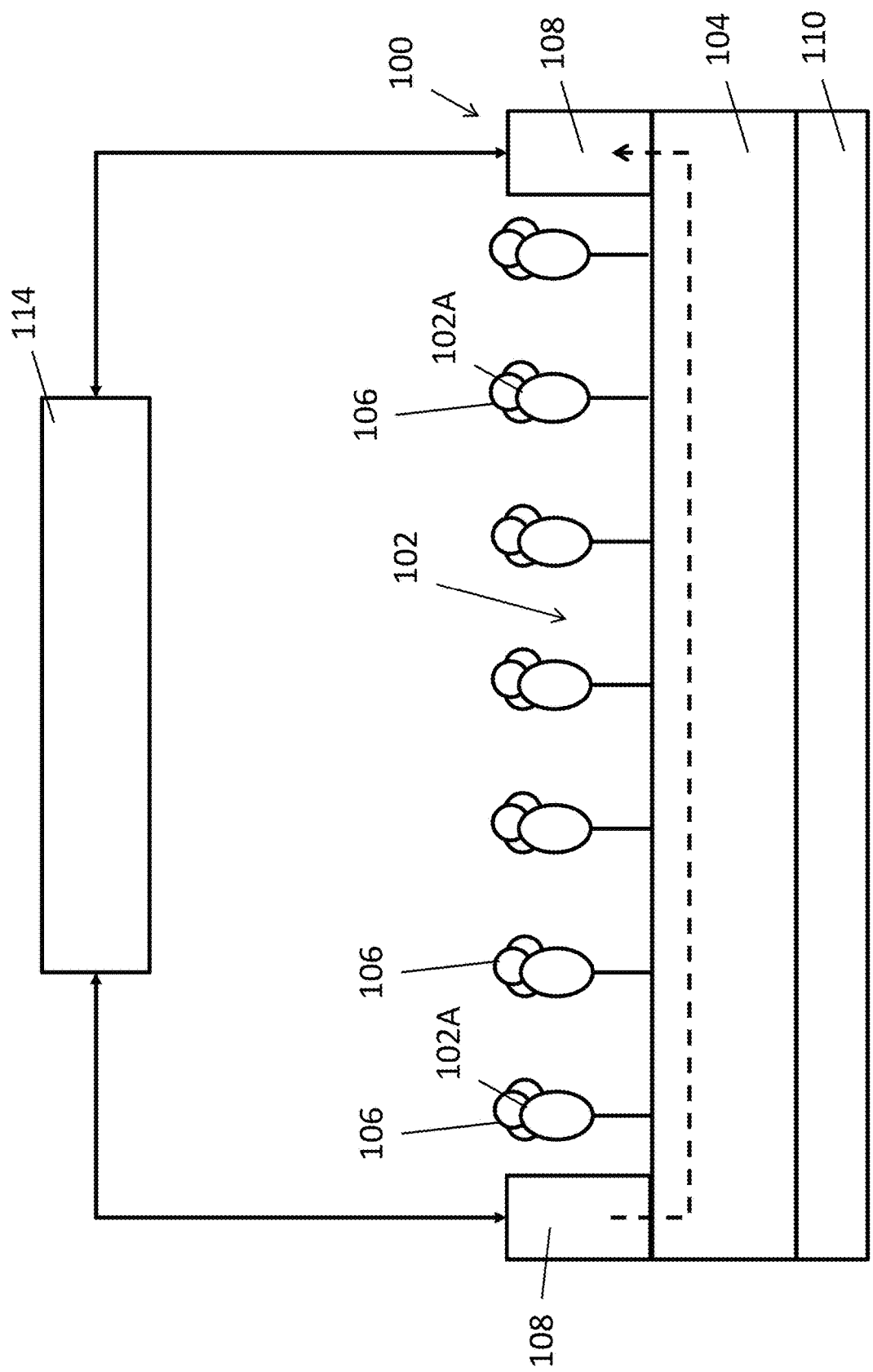
FIG. 8 is an illustration of detecting a target substance by using the electrochemical detector of FIG. 7A.

With reference to FIGS. 7A, 7B and 8, there is shown an example of detecting a target substance 106 using an electrochemical detector 100. In this example, an electrochemical detector 100 is exposed to the target substance 106. By applying a voltage or a current bias across the two electrodes 108, the current-voltage characteristic of the electrochemical detector 100 under the influence of target substance 106 can be obtained. Different amount or concentration of the target substance 106 may then be determined based on the different current-voltage characteristic obtained. In some examples, the current-voltage characteristic may be characterized as an electrical resistance/impedance value across the two electrodes 108, which means that the amount of target substance 106 detected is represented by the change of resistance/impedance of the electrochemical detector 100.

Since the substance selection layer 102 may be electrically conductive or non-conductive, therefore the change of resistance/impedance of the electrochemical detector 100 may be an increase or a decrease based on the conductivity of the substance selection layer 102 deposited on the semiconductor layer. For example, an accommodation of target substance molecule in a conductive MIP layer 102 may result in a decrease in a resistance/impedance of the combination of the substance selection layer 102 and the semiconductor layer.

Alternatively, an accommodation of target substance molecule in a conductive MIP layer 102 may result in an increase or decrease in a resistance/impedance of the semiconductor layer due to an electric field effect induced to the semiconductor layer by the MIP layer 102 accommodated with the substance molecules.

Referring to FIG. 7B, the substance selection structures may only selectively interact with the target substance 106 but not any other substances 112. Whereupon the MIP interact with the target substance 106, the voids 102A in the MIP layer 102 temporally or permanently accommodates molecules of the target substance 106 which may effectively change the electrical resistance and/or the charging state of the MIP layer. As a result, the current-voltage characteristic of the combination of the MIP layer 102 and semiconductor layer 104 underneath may be altered, this may include a change of conductivity of the semiconductor layer 104 due to the changed electric field of the adjacent MIP layer 102 and/or the conductivity of the layer of MIP layer, hence the electrical resistance across the semiconductor layer 104 and/or MIP layer 102 are altered. By using suitable measurement apparatus such as an electrical multimeter 114 or a semiconductor parameter analyser, the electrical characteristic of the electrochemical detector 100 may be determined.

These embodiments are advantageous in that the active layer of the electrochemical detector only includes two layers of material, such that the structure and hence the fabrication of the detector is kept simple, which enhance the yield and stability of the performance of the fabricated detectors. The thin film structure also minimizes the required amount to fabricate the electrochemical detector. In addition, the fabrication only requires low-cost materials and processing techniques such that large scale fabrication process is favourable.

Advantageously, the electrochemical detector is based on selective bonding to detect biogenic amines in vapour phase. Therefore, such sensor may be used to detect extremely low levels (ppb) of biogenic amines with appropriate detection layer, the electrochemical detector may be used as a cost-effective, accurate and reliable means for biogenic amines in air to evaluate the quality of food.

In addition, a wide range of appropriate substance selection structure or the MIP layer 102 may be included in the electrochemical detector, this enable the electrochemical detector may be used for the detection of a wide range of target substances. Since the detection is based on selective interaction between the MIP layer 102 and the target substances, the detector may be used to detect extremely low levels or concentrations (down to ppb level) of target chemicals. This also enable the electrochemical detector may be used for gas leak detector.

Figure 9A:
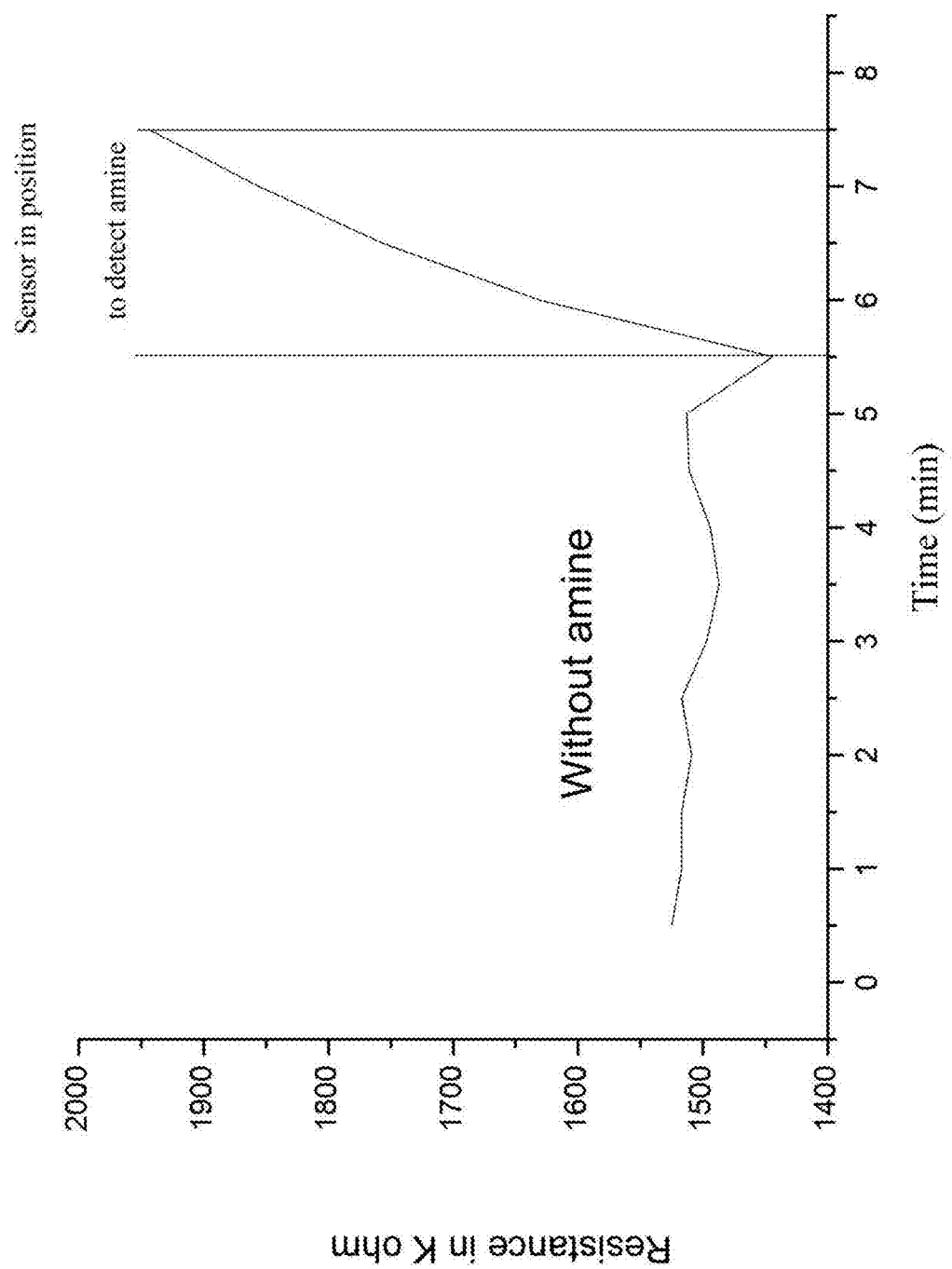
FIGS. 9A and 9B are plot showing responses of electrochemical detector of FIG. 1 exposed to a target substance.
Figure 9B:
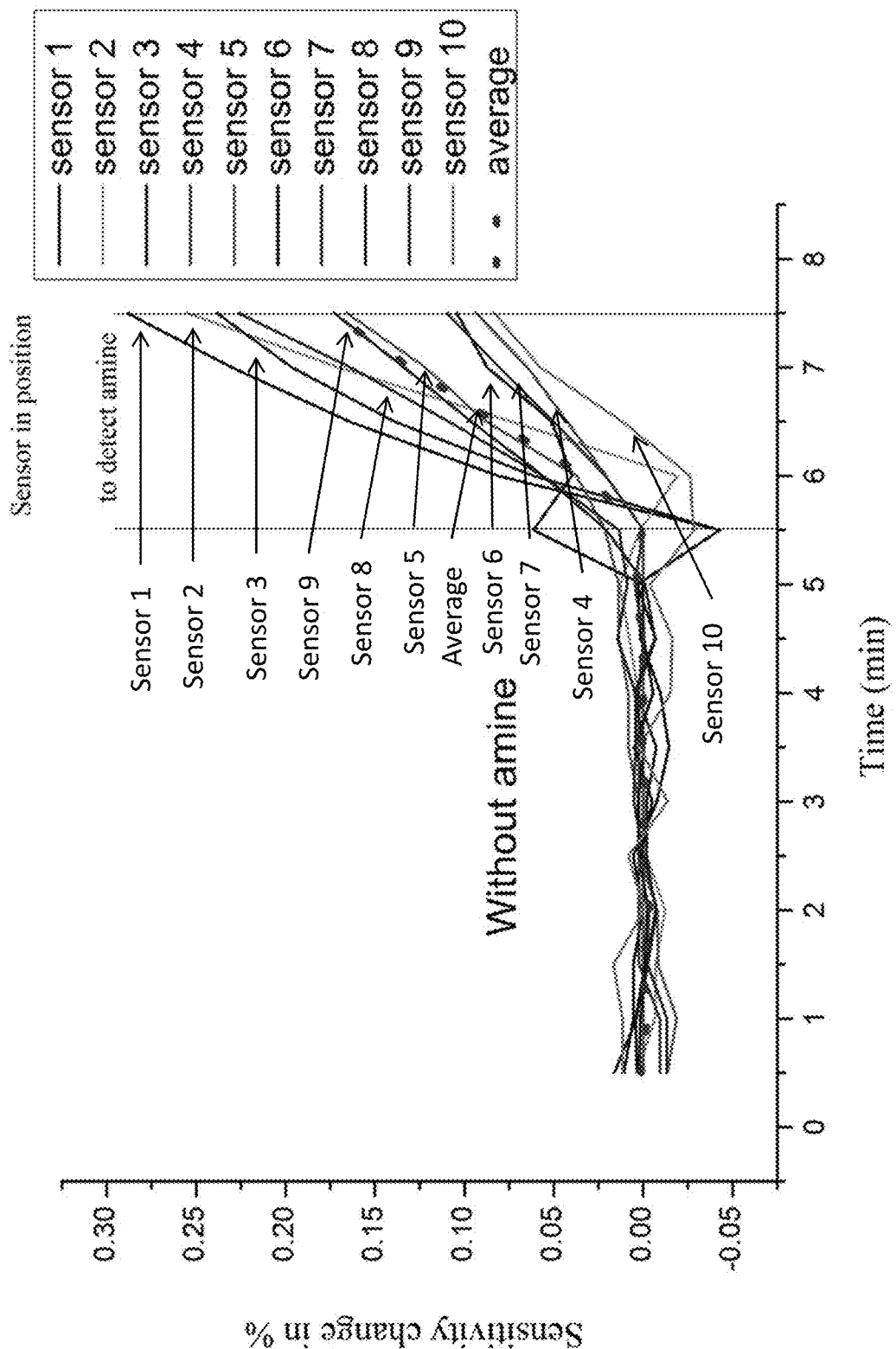

With reference to FIGS. 9A and 9B, there is shown two plots of a response of the electrochemical detector in accordance with the embodiments of the invention. The experimental setup is similar to the example as shown in FIG. 8. For each experiment, the electrochemical detector was first stabilized in an atmosphere condition, and the analyte with the amine target substance (concentration in ppb level) was put proximate to the detector after the reading (resistance) is stable. When the analyte is placed close to the detector, the resistance value increased.

Alternatively, the electrochemical detector may be used to detect target substances in liquid phase target.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

The invention claimed is:

1. An electrochemical detector comprising:
 a substance selection layer disposed on a semiconductor layer;
 a substrate including an insulating material, the substrate disposed under the semiconductor layer such that the substrate is opposite the substance selection layer with respect to the semiconductor layer; and
 only two electrodes, each disposed on or above the substance selection layer thereby forming a two-terminal device;
 wherein the substance selection layer includes a polymer layer functionalized with dioxaborinane and crown ether groups for accommodating at least one molecule of a target substance so as to alter an electrical characteristic of the semiconductor layer, and wherein the insulating material includes at least one of polymer, glass and ceramic.

2. An electrochemical detector in accordance with claim 1, wherein the target substance includes an amine.

3. An electrochemical detector in accordance with claim 2, wherein the target substance includes a biogenic amine.

4. An electrochemical detector in accordance with claim 1, wherein the polymer layer includes a plurality of voids each adapted to accommodate each of the at least one molecule of the target substance.

5. An electrochemical detector in accordance with claim 4, wherein each of the plurality of voids includes a structure matching with a molecular structure of the at least one molecule of the target substance.

6. An electrochemical detector in accordance with claim 5, wherein the plurality of voids are selective to the target substance.

7. An electrochemical detector in accordance with claim 1, wherein the polymer layer includes a molecular imprinted polymer.

8. An electrochemical detector in accordance with claim 7, wherein the molecular imprinted polymer includes a plurality of polymer particles each having a size of around 50 μm.

9. An electrochemical detector in accordance with claim 1, wherein the substance selection layer is electrically conductive.

10. An electrochemical detector in accordance with claim 1, wherein the substance selection layer is electrically non-conductive.

11. An electrochemical detector in accordance with claim 1, wherein an electrical characteristic of a combination of the substance selection layer and the semiconductor layer is altered when the polymer layer accommodates the at least one molecule of the target substance.

12. An electrochemical detector in accordance with claim 11, wherein an electrical impedance of a combination of the substance selection layer and the semiconductor layer is altered.

13. An electrochemical detector in accordance with claim 1, wherein the semiconductor layer includes at least one of an organic semiconductor, a polymer semiconductor, small molecules, an oxide-based semiconductor and a silicon-based semiconductor.

14. An electrochemical detector in accordance with claim 1, wherein the substrate is a flexible substrate.

15. An electrochemical detector in accordance with claim 1, wherein the semiconductor layer, the substance selection layer and the two electrodes are based on organic materials and/or metal oxide.

16. An electrochemical detector in accordance with claim 1, wherein the semiconductor layer has a thickness of 10 nm-200 nm.

17. An electrochemical detector in accordance with claim 1, wherein the two electrodes are spaced at a distance in a range of around 50 μm to 1000 μm.

18. A method of fabricating the electrochemical detector in accordance with claim 1, comprising steps of:
 depositing the semiconductor layer on the substrate, the substrate including the insulating material, wherein the insulating material includes the at least one of polymer, glass and ceramic; and
 depositing the substance selection layer on the semiconductor layer, wherein the substance selection layer includes the polymer layer functionalized with dioxaborinane and crown ether groups; and
 depositing layers of electrical conductive material to provide the two electrodes on or above the semiconductor layer.

19. A method of fabricating the electrochemical detector in accordance with claim 18, wherein the step of depositing the substance selection layer on the semiconductor layer comprises steps of:
 fabricating a combination of a molecular-imprinted polymer and a molecular template of the target substance using a polymerization process;
 extracting and removing the molecular template from the molecular-imprinted polymer; and depositing the molecular-imprinted polymer on the substrate.

20. A method for fabricating the electrochemical detector in accordance with claim 19, wherein the step of depositing the substance selection layer on the semiconductor layer further comprises a step of grounding and sieving the combination of the molecular-imprinted polymer and the molecular template to obtain a plurality of polymer particles each having a size of around 50 µm.

21. A method of fabricating the electrochemical detector in accordance with claim 18, wherein the steps of depositing the semiconductor layer, the substance selection layer and/or the layers of electrical conductive material involve a solution process.

22. A method of fabricating the electrochemical detector in accordance with claim 21, wherein the solution process involve spin coating and/or printing, wherein the solution process of printing further includes pad printing and/or silk screening.

23. A method of detecting a target substance, comprising steps of:
    exposing the electrochemical detector in accordance with claim 1 to the target substance;
    applying a voltage and/or a current bias across the two electrodes; and
    determining an amount of target substance detected based on a current-voltage characteristic of the electrochemical detector exposed to the target substance.

24. A method of detecting a target substance in accordance with claim 23, wherein the step of determining an amount of target substance detected based on the current-voltage characteristic of the electrochemical detector exposed to the target substance includes determining a change of electrical resistance across the two electrodes of the electrochemical detector.

25. A method of detecting a target substance in accordance with claim 23, wherein the determined amount of target substance is further associated with a quality of food.

* * * * *